(12) United States Patent
Gravina et al.

(10) Patent No.: US 7,662,576 B2
(45) Date of Patent: Feb. 16, 2010

(54) METHOD FOR IDENTIFYING ESTER COOLERS

(75) Inventors: Stephen Anthony Gravina, Rutherford, NJ (US); Jason Michael Montez, Rumson, NJ (US); Vijyeta Kapur, Monroe, NJ (US); Carrie Ann Maxwell, Brick, NJ (US); Mark L. Dewis, Matawan, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 11/951,793

(22) Filed: Dec. 6, 2007

(65) Prior Publication Data

US 2009/0148938 A1   Jun. 11, 2009

(51) Int. Cl.
*G01N 33/68* (2006.01)
*C07K 14/435* (2006.01)
*C07K 14/705* (2006.01)

(52) U.S. Cl. .................. 435/7.2; 530/350; 536/23.5

(58) Field of Classification Search ................ None
See application file for complete search history.

(56) References Cited

U.S. PATENT DOCUMENTS

| | | |
|---|---|---|
| 7,018,617 B1 | 3/2006 | Tracey, Jr. et al. |
| 2005/0202539 A1 | 9/2005 | Chong et al. |
| 2005/0265930 A1 | 12/2005 | Erman et al. |
| 2006/0142547 A1 | 6/2006 | Bevan et al. |

FOREIGN PATENT DOCUMENTS

WO    WO 2005089206 A2 *  9/2005

OTHER PUBLICATIONS

NCBI Accession No. Y10601 [gi:4165268] with Revision History—Jun. 30, 1998-Apr. 18, 2005.
NCBI Accession No. NM_007332 [gi:116534989] with Revision History—Dec. 18, 1999-Sep. 25, 2007.
Bianchi et al., "Application of Large-Scale Transiently Transfected Cells to Functional Assays of Ion Channels:Different Targets and Assay Formats", ASSAY and Drug Development Technologies 2007 5:417-424.
Hinman et al., "TRP channel activation by reversible covalent modification", Proc Natl Acad Sci 2006 103 (51):19564-19568.
Jordt et al., "Mustard oils and cannabinoids excite sensory nerve fibres through the TRP channel ANKTM1", Nature 2004: 417:260-265.
Macpherson et al., "Noxious compounds activate TRPA1 ion channels through covalent modification of cysteines", Nature 2007 445:541-545.
Sawada et al., "Cold sensitivity of recombinant TRPA1 channels", Brain Research 2007 1160:39-46.
Smith et al., "Cold-sensitive, menthol-insensitive neurons in the murine sympathetic nervous system", NeuroReport 2004 15(9):1399-1403.

* cited by examiner

*Primary Examiner*—Manjunath N. Rao
*Assistant Examiner*—Jon M Lockard
(74) *Attorney, Agent, or Firm*—Licata & Tyrrell P.C.

(57) ABSTRACT

The Transient Receptor Potential Cation Channel, Subfamily A, Member 1 (TRPA1) protein has been identified as an ester cooler receptor and therefore is useful in screening assays for identifying ester coolers, in particular ester coolers with a relative cooling strength which exceeds (−)−menthol.

2 Claims, 5 Drawing Sheets

METHOD FOR IDENTIFYING ESTER COOLERS

BACKGROUND OF THE INVENTION

Transient Receptor Potential Cation Channel, Subfamily A, Member 1 (TRPA1) protein has been characterized as a cold-activated channel with a lower activation temperature than the cold and menthol receptor, Transient Receptor Potential Cation Channel, Subfamily M, Member 8 (TRPM8) (Story, et al. (2003) Cell 112:819-829; McKemy ((2005) *Molecular Pain* 1:16). TRPA1 is a distant family member of TRP channels that shares little amino acid similarity with TRPM8. It is found in a subset of nociceptive sensory neurons where it can be coexpressed with the capsaicin/heat receptor, TRPV1, but not TRPM8. Consistent with the expression pattern of TRPA1, it has been identified on noxious cold-sensitive sensory neurons that also respond to capsaicin but not to menthol. It has also been demonstrated that mustard oil (allyl isothiocyanate) activates TRPA1 (Jordt, et al. (2004) *Nature* 427:260-265; Sawada, et al. (2007) *Brain Research* 1160:39-46). Moreover, the mouse TRPA1 channel is activated by pungent natural compounds present in cinnamon oil (cinnamaldehyde), wintergreen oil (methyl salicylate), clove oil (eugenol), and ginger (gingerol) (Bandell, et al. (2004) *Neuron* 41:849-857), wherein TRPA1 activation by cold temperature may convey a paradoxical burning pain sensation. In experiments in male Sprague-Dawley rats, it was demonstrated that pharmacologic blockade of TRPA1 by anti-nerve growth factor (NGF), p38 MAPK inhibitor, or TRPA1 anti-sense oligodeoxynucleotide in primary sensory neurons reversed cold hyperalgesia caused by inflammation and nerve injury (Obata, et al. (2005) *J. Clin. Invest.* 115: 2393-2401).

In this regard, compositions and methods associated with TRP and TRP-like channels are provided in U.S. Pat. No. 7,018,617 and U.S. Patent Application Nos. 20060142547 and 20050202539

SUMMARY OF THE INVENTION

The present invention is a method for identifying an ester cooler. The method involves contacting a Transient Receptor Potential Cation Channel, Subfamily A, Member 1 (TRPA1) protein with test agents; determining whether the test agents modulate the activity of the TRPA1; and selecting for TRPA1 modulators that have a relative cooling strength which exceeds menthol thereby identifying an ester cooler. In one embodiment, the TRPA1 protein has an amino acid sequence as set forth in SEQ ID NO:1. In another embodiment, the determining step is carried out in vitro. In a further embodiment, the determining step is carried out in vivo. Agents identified by the method are also provided as is a host cell which expresses the TRPA1 protein set forth in SEQ ID NO:1.

BRIEF DESCRIPTION OF THE DRAWINGS

FIG. 3 shows the synergistic response of TRPM8 to a blend of coolers composed of Menthol and WS-3, wherein the concentrations of Menthol (FIG. 3A) and WS-3 (FIG. 3B) were varied.

DETAILED DESCRIPTION OF THE INVENTION

Menthol exists abundantly in nature and has been known for a long time as a physiological cooling compound. It is well-established that the "cooling" effect of menthol is a physiological effect. Menthol has been used widely in cigarettes, cosmetics, toothpastes, chewing gum, sweets, and medicines. Disadvantages of menthol include its strong "stinging" smell, bitter taste, burning sensation in high concentration and high volatility. These undesirable properties limit applications of menthol to some extent. Substitutes of menthol have been actively sought. One class of suitable substitutes include the ester coolers, i.e., esters which exhibit a physiological cooling effect.

Transient Receptor Potential Cation Channel, Subfamily A, Member 1 (TRPA1) protein, also known as Ankyrin-Like Protein with Transmembrane Domains 1 (ANKTM1), has now been identified as the receptor which binds ester coolers such as cooler 2 and ultracool 7. Thus, the present invention relates to the TRPA1 protein, nucleic acid molecules that encode the TRPA1 protein, vectors containing the nucleic acid molecules which encode the TRPA1 protein, and cells which express the TRPA1 protein. The invention further relates to assay systems using the TRPA1 protein, assay systems using the cells which express the TRPA1 protein, and compounds identified using the assay systems.

Assay systems of the present invention are of particular use in identifying agonists and antagonists which modulate the activity of TRPA1. Moreover, assay systems of the invention can be used to identify or design blends of modulators that have improved properties. Modulators, and blends thereof, of particular interest include those with improved properties such as all natural, longer lasting and higher potency compared to conventional cooling agents such as menthol.

In particular embodiments of the present invention, the TRPA1 protein as used in accordance with the present invention has an amino acid sequence as set forth in SEQ ID NO:1. This TRPA1 protein, identified under GENBANK Accession No. NM_007332, shares significant C-terminal sequence identity with the *Homo sapiens* ankyrin-like protein set forth in GENBANK Accession No. Y10601 (Bandell, et al. (2004) supra). The TRPA1 protein is composed of several domains including akryrin repeats, which mediate protein-protein interactions, located at residues 95 to 218, 233 to 362, 336 to 502, 476 to 600 and an ion transport domain located at residues 796 to 959.

The TRPA1 protein of the invention can be a wild-type protein or a modified TRPA1 protein, i.e., a TRPA1 that has one or more modifications in the amino acid sequence. As such, the TRPA1 protein may be modified in whole or in part. These modifications in the amino acid sequence include mutations of one or more amino acids, insertion of one or more amino acids, deletion of one or more amino acids, and substitutions of one or more amino acids in which one or more amino acids are deleted and one or more amino acids are added in place of the deleted amino acids.

Amino acid substitutions may also be introduced to substitute an amino acid with a particularly preferable property. For example, a Cys may be introduced as potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

In this regard, it has been noted that the diverse chemical nature of TRPA1-activating irritants suggests that their reactivity is critical in TRPA1 activation (Hinman, et al. (2006) *Proc. Nat. Acad. Sci.* 103:19564-19568). By examining *Xenopus oocytes* expressing wild-type and mutant human TRPA1, it was found that structurally distinct environmental irritants activated TRPA1 by a reversible covalent modification of cysteine residues at positions 619, 639, and 663 (and to a lesser extent Lys708) within the cytoplasmic N-terminal domain of the channel.

Similarly, Macpherson, et al. (2007) *Nature* 445:541-545) observed that most compounds known to activate TRPA1 are able to covalently bind cysteine residues. Click chemistry was used to show that derivatives of two such compounds, mustard oil and cinnamaldehyde, covalently bind mouse TRPA1. Structurally unrelated cysteine-modifying agents such as iodoacetamide (IA) and (2-aminoethyl)methanethiosulfonate (MTSEA) also bind and activate TRPA1.

Therefore, certain embodiments of the present invention embrace mutant TRPA1 proteins containing one or more mutations at amino acid residues 621, 641, 665, and 710 of SEQ ID NO:1. Such mutants can be used in the identification of TRPA1 modulators, as well as in the determination of how TRPA1 modulators agonize or antagonize TRPA1. As may be shown by standard receptor binding assays, the modified TRPA1 protein is essentially indistinguishable from the wild-type counterpart except for possible differences in binding affinity for ligands, activation, and signal transduction.

Truncated TRPA1 proteins are also embraced by the present invention. Truncated TRPA1 proteins include TRPA1 proteins as set forth in SEQ ID NO:1, wherein said proteins lack one or more amino acid residues at the N-terminus, C-terminus, or both. In this regard, one embodiment embraces a truncated TRPA1 protein lacking one or more akyrin repeat domains located at the N-terminus. In another embodiment, the truncated TRPA1 protein lacks the ion transport domain located at the C-terminus. In certain embodiments, the truncated TRPA1 protein is composed of residues 601 to 795 of SEQ ID NO:1. It is contemplated that truncated TRPA1 proteins find application in ligand binding assays as well as in the identification of proteins which interact with TRPA1.

Modified, truncated, and wild-type TRPA1 proteins can be generated by molecular biological techniques standard in the genetic engineering art, including but not limited to, polymerase chain reaction (PCR), site-specific mutagenesis, restriction enzyme digestion, ligation into an expression vector or plasmid, introduction into a host cell and recombinant protein expression, as well as chemical synthesis. Such technology generally involves isolating a nucleic acid molecule encoding the protein of interest, e.g., by PCR-amplification of the coding sequence, inserting the isolated nucleic acid into an expression vector, which contains all the necessary transcriptional and translational control sequences for expressing the TRPA1 protein in a host cell, and introducing the expression vector into a host cell for recombinant TRPA1 protein expression.

In particular embodiments of the present invention, a nucleic acid molecule encoding a TRPA1 protein as set forth in SEQ ID NO:1 is employed. In certain embodiments, the nucleic acid molecule is set forth in SEQ ID NO:2. It should be appreciated that also within the scope of the present invention are nucleic acid molecules encoding TRPA1 having the same amino acid sequence as SEQ ID NO:1, but which are degenerate to SEQ ID NO:2. By "degenerate to" is meant that a different three-letter codon is used to specify a particular amino acid.

Conventional molecular biology, microbiology, and recombinant DNA techniques for achieving TRPA1 protein expression are routinely practiced in the art using commercially available reagents, expression vectors, and host cells. Such techniques are explained fully in the literature. See, e.g., Sambrook, et al. (1989) *Molecular Cloning: A Laboratory Manual*; Ausubel, (1994) *Current Protocols in Molecular Biology*, Volumes I III; Gait (1984) *Oligonucleotide Synthesis*; Freshney (2000) *Animal Cell Culture*; and Perbal (1984) *A Practical Guide To Molecular Cloning*.

For the purposes of the present invention, a DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

A wide variety of host/expression vector combinations can be employed in expressing a TRPA1 protein of this invention. Useful expression vectors include, for example, derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage lambda, e.g., NM989, and other phage DNA, e.g., M13 and filamentous single stranded phage DNA; yeast plasmids such as the 2 μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences can be used in these vectors to express a TRPA1 protein of this invention. Transcriptional and translational control sequences, also referred to expression control sequences, are DNA regulatory sequences, such as promoters, enhancers, polyadenylation signals, terminators, and the like, that are operatively linked to the TRPA1 nucleic acid molecule to provide for the expression of the TRPA1 protein in a host cell. A DNA molecule is operatively linked to expression control sequences when the expression control sequence controls and regulates the transcription and translation of that DNA molecule. The term "operatively linked" includes having an appropriate start signal (e.g., ATG) in front of the DNA molecule to be expressed and maintaining the correct reading frame to permit expression of the DNA molecule under the control of the expression control sequence and production of the desired product encoded by the DNA molecule.

Such useful expression control sequences include, for example, the early or late promoters of SV40, CMV, vaccinia, polyoma or adenovirus, the lac system, the trp system, the TAC system, the TRC system, the LTR system, the major operator and promoter regions of phage lamda, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof In selecting an expression control sequence, a variety of factors will normally be considered. These include, for example, the relative strength of the system, its controllability, and its compatibility with the particular DNA molecule or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA molecules to be expressed, and the ease of purification of the expression products.

A signal sequence can also be included before the coding sequence. A signal peptide is sequence located N-terminal to the protein of interest, which communicates to the host cell to direct the protein to the cell surface or secrete the protein into the media. The signal peptide is clipped off by the host cell before the protein leaves the cell. Signal sequences can be found associated with a variety of proteins native to prokaryotes and eukaryotes.

The TRPA1 protein can also be expressed as a fusion protein to aid in stability, purification, or detection of the TRPA1 protein. For example, protein tags such as His6, FLAG, c-Myc and the like can be fused to the TRPA1 protein to aid in protein purification and detection. In some embodiments, the TRPA1 protein is fused to a detectable molecule. In this regard, a "detectable molecule" means any molecule capable of detection by spectroscopic, photochemical, biochemical, immunochemical, radiochemical, electrical, and optical means, including but not limited to, fluorescence, phosphorescence, radioactivity, and bioluminescence. Detectable molecules include, but are not limited to green fluorescent protein (GFP), yellow fluorescent proteins (YFP), red fluorescent proteins (RFP), cyan fluorescent proteins (CFP), luciferase, rhodamine-conjugated antibody, chloramphenicol acetyl transferase (CAT), and the like.

A wide variety of unicellular host cells are also useful in expressing a TRPA1 protein of this invention. These hosts can include well-known eukaryotic and prokaryotic hosts, such as strains of *E. coli, Pseudomonas, Bacillus, Streptomyces*, fungi such as yeasts, plant cells, nematode cells, and animal cells, such as CHO, R1.1, B-W and L-M cells, African Green Monkey kidney cells (e.g., COS 1, COS 7, BSC1, BSC40, and BMT10), insect cells (e.g., Sf9), and human cells (e.g., HEK-293), and plant cells in tissue culture.

A host cell has been transformed with an exogenous nucleic acid molecule (e.g., an expression vector) when such nucleic acid molecule has been introduced inside the cell. The transforming nucleic acid molecule may or may not be integrated (covalently linked) into chromosomal DNA making up the genome of the cell. In prokaryotes, yeast, and mammalian cells for example, the transforming nucleic acid molecule may be maintained on an episomal element such as a plasmid or transiently transfected. With respect to eukaryotic cells, a stably transformed cell is one in which the transforming nucleic acid molecule has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Once introduced into the host cell, an expression vector harboring a nucleic acid molecule encoding TRPA1 can be induced to express the TRPA1 protein (e.g., when the TRPA1 is expressed from an inducible promoter). Alternatively, the TRPA1 protein can be constitutively expressed. Depending on the screening assay, the TRPA1 protein can be purified from the host cell or host cell culture medium and used in in vitro assay. Such purification can be achieved using conventional purification methods including column chromatography (e.g., affinity chromatography), gel electrophoresis and the like. Alternatively, the screening assay can be carried out in vivo using the host cell which expresses the TRPA1 protein.

The purified and isolated TRPA1 proteins of the present invention are useful in cell-free or in vitro assays for identifying agents which modulate the activity of TRPA1. A typical screening assay using TRPA1 protein involves contacting the TRPA1 protein with one or more test agents, and determining whether the test agents modulate the activity of TRPA1, wherein activity in this context includes binding of the test agents to TRPA1. In certain embodiments, cell-free assays are carried out by depositing TRPA1 protein on a substrate, wherein the substrate can be any artificial substrate including, but not limited to, glass, plastic, diamond, ceramic, semiconductor, silica, fiber optic, diamond, biocompatible monomer, biocompatible polymer, polymer beads (including organic and inorganic polymers), and the like. Methods of the present invention that use the TRPA1 proteins provide sensitive assays and can provide for enhanced detection, for example, of agonists with relative cooling strengths which exceed menthol. In this regard, cell-free assays can also be used to determine whether TRPA1 has a higher binding affinity for a test agent as compared to other known ester coolers which bind TRPA1, e.g., Cooler 2 or Ultracool7.

In particular embodiments, the present invention provides for a cell-based or in vivo method for identifying ester coolers which modulate the activity or activation of TRPA1. In accordance with this method, a host cell expressing a recombinant TRPA1 protein is contacted with one or more test agents and the ability of the test agents to modulate the activity of TRPA1 is determined. Activity of TRPA1 in the cell-based assay can be determined using a variety of techniques. For example, one embodiment embraces the use of a calcium influx assay to determine whether a test agent increases or decreases the activity of TRPA1 as compared to menthol, or alternatively WS-3 (Bianchi, et al. (2007) *Assay Drug Dev. Technol.* 5(3): 417-24; Smith, et al. (2004) *NeuroReport* 15:1399-1403). In particular embodiments, a fluorometric imaging plate reader (FLIPR) is employed to quantify the calcium-imaging responses of test agents.

In another embodiment, the membrane potential of the cell is used as an indicator of TRPA1 activity (Bianchi, et al. (2007) supra). In accordance with this embodiment, membrane potential is determined by detecting a change in fluorescence of a dye whose fluorescence is dependent upon cell polarization. Such dyes are routinely used in the art.

In still a further embodiment, the reversible covalent modification of cysteine residues can be used as an indicator of whether the test agent binds to TRPA1. In this regard, activation of TRP channels such as TRPC1, TRPC4, TRPC5, TRPV1, TRPV3 and TRPV4 has been shown to be mediated by cysteine S-nitrosylation (Yoshida, et al. (2006) *Nat. Chem. Biol.* 2:596-607). Accordingly, the detection of post-translation modification, e.g., nitrosylation of cysteine residues would be indicative of activation by a test agent. Nitrosylation can be detected by conventional methods of using an antibody which specifically recognizes a TRPA1 protein nitrosated at one or more cysteine residues.

Preferred assays to measure TRPA1 channel activity are cell-based assays that utilize cells loaded with ion or voltage-sensitive dyes to report TRPA1 activation. By way of illustration, an inducible TRPA1 cell line was created by stably introducing TRPA1 into TREX-FLPN cells (INVITROGEN). The inducible system avoids potential toxic side effects of stably transfected TRPA1 previously reported (Jaquemar et al. (1999) 274:7325-7333). In this assay, cells were incubated with a suitable flouroscent dye. Microplates were then read in a FLIPR tetra at excitation wavelength of 470-495 and an emission wavelength of 515-575. After obtaining a baseline, various cooling compounds were added and fluorescence measured for several minutes.

Screening assays using the TRPA1 proteins of the present invention are useful for identifying agents which are TRPA1 ligands, agonists, antagonists, inverse agonists, desensitization compounds, and the like. In this regard a test agent which increases TRPA1 protein activity is indicative of an agent having TRPA1 agonist activity; whereas a test agent that decreases TRPA1 protein activity is indicative of an agent having TRPA1 antagonist activity. It is contemplated that agonists find application in providing cooling effects to food products, pharmaceutical compositions, hygiene products, etc. and antagonists may be useful in the treatment or amelioration of, e.g., pain associated with noxious cold.

Test agents which can be screened in accordance with the method of the present invention are generally derived from libraries of agents or compounds. Such libraries can contain either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Alternatively, known ester coolers can be screened for their ability to modulate the activity of TRPA1. Examples of ester coolers which can be specifically screened are disclosed in U.S. Pat. No. 7,189,760. Moreover, ester derivatives or analogs of known cooling agents can be screened in accordance with the present invention. Examples of agent mixtures include, but are not limited to, extracts of prokaryotic or eukaryotic cells and tissues, as well as fermentation broths and cell or tissue culture supernates. In particular embodiments, blends of test agents are assayed. Databases of chemical structures are also available from a number of sources including Cambridge Crystallographic Data Centre (Cambridge, UK) and Chemical Abstracts Service (Columbus, Ohio). De novo design programs include Ludi (Biosym Technologies Inc., San Diego, Calif.), Sybyl (Tripos Associates) and Aladdin (Daylight Chemical Information Systems, Irvine, Calif.).

Library screening can be performed using any conventional method and can be performed in any format that allows rapid preparation and processing of multiple reactions, including high throughput formats. For in vitro and in vivo screening assays, stock solutions of the test agents as well as assay components can be prepared manually and all subsequent pipeting, diluting, mixing, washing, incubating, sample readout and data collecting carried out using commercially available robotic pipeting equipment, automated work stations, and analytical instruments for detecting the signal generated by the assay. Examples of such detectors include, but are not limited to, luminometers, spectrophotometers, and fluorimeters, and devices that measure the decay of radioisotopes.

Agents of particular interest are ester coolers which exhibit a cooling effect. Because the use of reported cooling threshold levels to estimate actual cooling strength can give erroneous results, relative cooling strengths compared to (−)-menthol can be employed to convey the cooling strength of a particular compound. Relative cooling strength values in accordance with the present invention can be determined on the basis of a sequential dilution method, i.e., a controlled dilution of samples to the concentration where their strength is about equal to a standard solution of (−)-menthol. For example, a 10 ppm solution of (−)-menthol is used as the standard solution and is assigned a standardized cooling strength value of 100. The corresponding relative cooling strengths for the individual cooling agents identified herein are then assigned based upon an organoleptic determination of the approximate concentration of cooling agent that is required to provide about the same cooling strength as the standardized 10 ppm solution of (−)-menthol. For example, Table 1 provides a list of common cooling agents and their relative cooling strengths compared to (−)-Menthol.

TABLE 1

| Cooling Agents | Relative Cooling Strengths* |
|---|---|
| (+)-Neoisomenthol | 3 |
| (−)-Neomenthol | 3 |
| (−)-Isomenthol | 3 |
| PMD 38 p-menthane-3,8-diol | 11 |
| (+)-Isomenthol | 11 |
| (−)-Neoisomenthol | 13 |
| (2R)-3-1-menthoxy)propane-1,2-diol | 15.8 |
| (2RS)-3-1-menthoxy)propane-1,2-diol | 22.5 |
| WS-30 (1-glyceryl p-menthane-3-carboxylate) | 22.5 |
| WS-4 (Ethyleneglycol p-menthane-3-carboxylate) | 23 |
| Coolact P (−)-isopulegol | 25 |
| (+)-Menthol | 27 |
| (+)-Neomenthol | 32 |
| (2S)-3-1-menthoxy)propane-1,2-diol | 39.5 |
| Frescolat MGA (menthyl lactate) | 41 |
| Frescolat ML (menthone glycerin acetal) | 43 |
| WS-14 (N-t-butyl-p-menthane-3-carboxamide) | 75 |
| WS-23 (2-Isopropyl-N,2,3-trimethylbutyramide) | 75 |
| (−)-Menthol | 100 |
| WS-12 (N-(4-methoxyphenyl)-p-menthane-3-carboxamide) | 150 |
| WS-3 (N-ethyl-p-menthane-3-carboxamide) | 150 |
| WS-5 (Ethyl 3-(p-menthane-3-carboxamido)acetate) | 400 |

*Compared to (−)-Menthol at 100. Source: Erman (2003) Presentation of the Society of Flavor Chemists, Perfumer & Flavorist 29: 34-50.

In addition to (−)-menthol, it is contemplated that other cooling agents can be used as a point of reference. Moreover, it is contemplated that the reference can be arbitrarily selected at, e.g., 1, 10, 100, 1000, etc. In this regard, U.S. Patent Application No. 20050265930 teaches that with respect to WS-3, with a relative cooling strength of 10.0, the relative cooling strength of highly purified WS-5 is about 16.7; WS-23 is about 5.0; Menthyl Lactate is about 2.9; WS-14 is about 5.0; WS-30 is about 1.5; N,2,2,6-Tetramethylcyclohexane-1-carboxamide is about 1.0; and monomenthyl glutarate is about 3.5.

Measurement of the cooling strength of one or more agents identified in accordance with the present method can be achieved using conventional methods. See, e.g., U.S. Patent Application No. 20050265930. By way of illustration, aqueous solutions of the cooling agent(s) are prepared, wherein each solution contains, e.g., 10 ppm of cooling agent(s). The solutions are organoleptically tested using a scale from, e.g., 0 (zero) to 100 of the cooling strength in comparison with the standard solution of 10 ppm of (−)-menthol, which is assigned a score of 100.

As indicated, ester coolers identified by the methods of the present invention can be used in any consumer good capable of using a cooling agent. Such consumer goods can be suitable for human consumption, or alternatively suitable for topical application to mammalian skin, including without limitation, human as well as veterinary applications. More specific examples of consumer goods include, without limitation, flavor blends, foods, cosmetic preparations, confectionery, soft and alcoholic beverages, chewing gums, toothpaste, dental floss, mouthwash, anti-plaque, anti-gingivitis compositions, shampoos, antidandruff shampoos, lotions, deodorants, after shave lotions, shaving gels, shaving aid composites, fragrances, skin sanitizing compositions, throat lozenges, throat drops, chewable antacid tablets, or pharmaceutical compositions or medications, including anti-inflammatory compositions, compositions for treatment of nasal symptoms, for upper gastrointestinal tract distress, for treating cold symptoms, for cough relief, for alleviating discomfort of hot flash, or for foot therapy, and the like.

The invention is described in greater detail by the following non-limiting examples.

EXAMPLE 1

FLIPR Assay

Materials. Fluo4NW solution was prepared by solubilizing one Fluo4NW bottle (Molecular Probes #F36206, component A) in 16 mL of Tyrode buffer (pH 7.4, 130 mM NaCl, 5 mM KCl, 2 mM $CaCl_2$, 1 mM $MgCl_2$, 5 mM $NaHCO_3$, 20 mM HEPES). To the resulting solution was then added 100 μL of water-soluble probenecid (Molecular Probes #F36206, component B).

Compounds tested included those listed in Table 2.

TABLE 2

| Compound | Structure |
|---|---|
| WS-3 | |
| Cooler 2 | |
| Cooler 3 | |
| Ultracool 7 | |
| Menthol | |
| Menthyl Lactate | |

Cell Preparation. Cells were trypsinized and 10,000 cells were dispensed per well in poly-lysine-coated, black, clear-bottom 384-well plates (35 μL/well in DMEM without antibiotics). Cells were incubated for 24 hours at 37° C. in 5% $CO_2$. The medium was completely eliminated and 20 (TRPA1) or 40 (TRPM8) μL/well of Fluo4NW solution was added to the plates. Cells were incubated for 1 hour at room temperature protected from light. Two addition kinetic measurements were recorded on the instrument for 7.5 (TRPA1) or 15 (TRPM8) minutes.

FLIPR Tetra Settings. Excitation wavelength was set at 470 to 495 nm, whereas emission wavelength was 515 to 575 nm.

EXAMPLE 2

TRPM8 FLIPR Analysis

Figure 1:
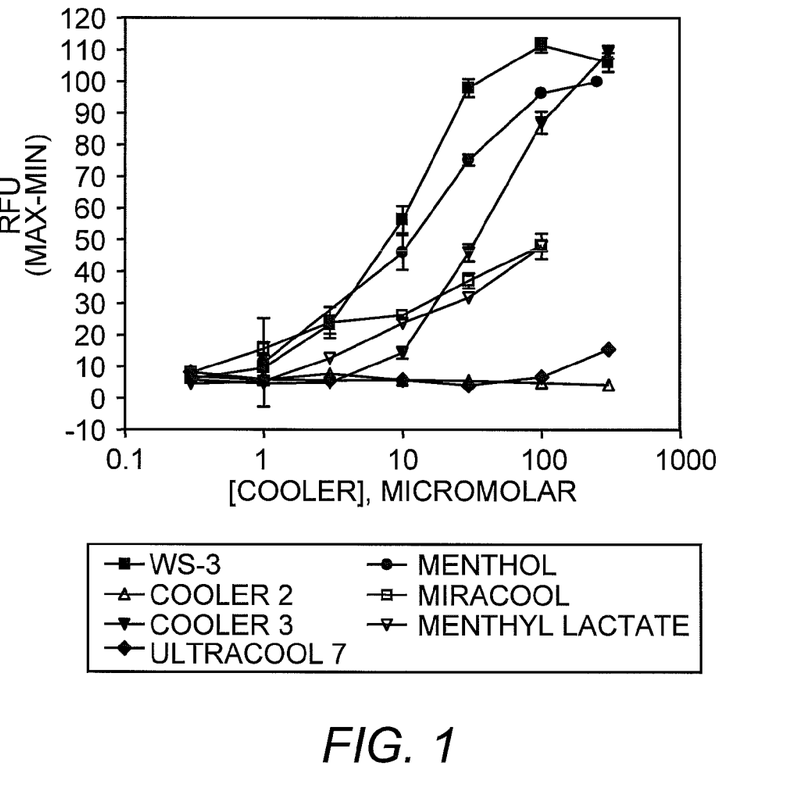
FIG. 1 shows a summary of the responses of TRPM8 to various coolers: WS-3, Cooler 2, Cooler 3, Ultracool 7, Menthol, Miracool, and Menthyl Lactate.
Figure 2:
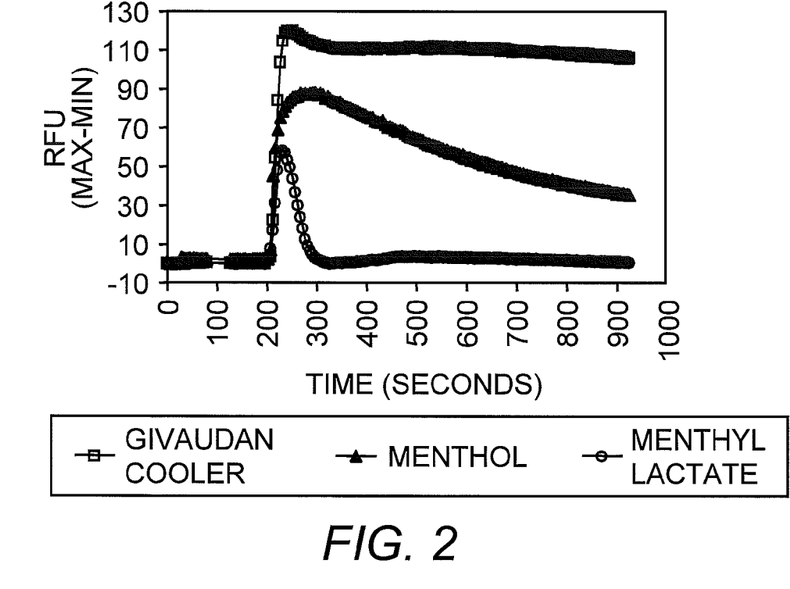
FIG. 2 shows the temporal responses of TRPM8 to Givaudan Cooler, Menthol, and Menthyl Lactate.
Figure 3A:
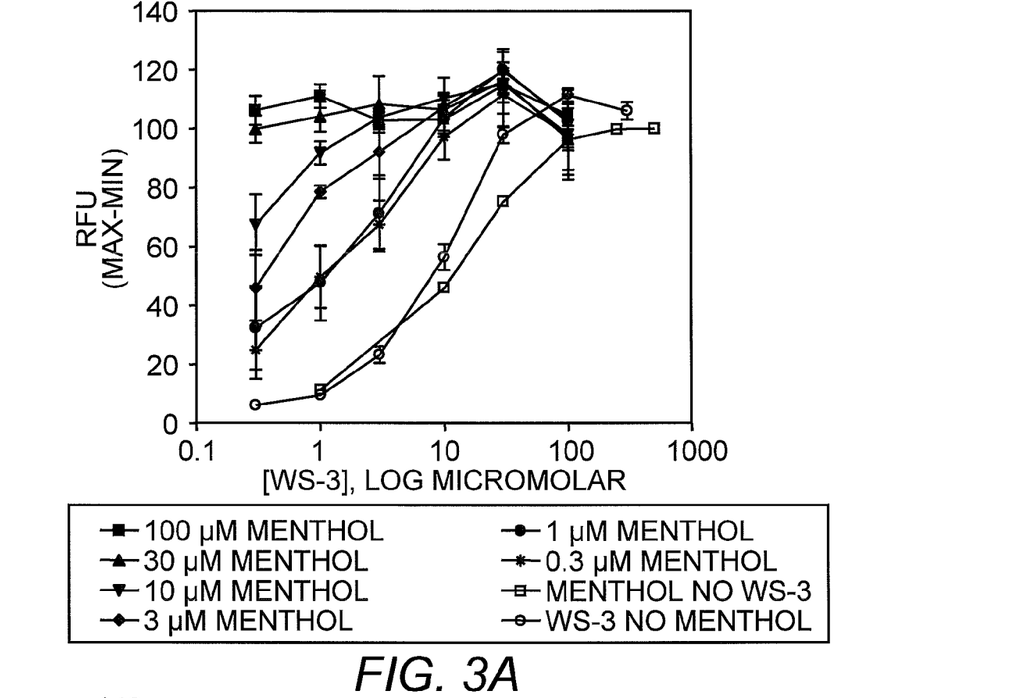
Figure 3B:
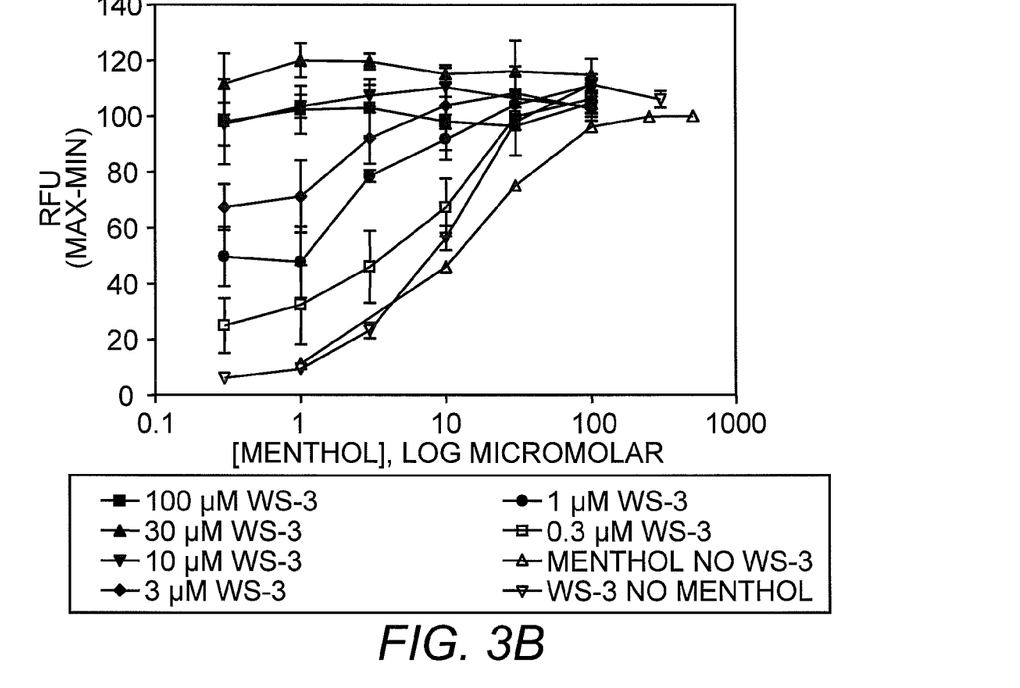

Results of TRPM8 FLIPR analysis indicated that the TRPM8 channel did not respond well to ester coolers such as Cooler 2 and Ultracool 7 (FIG. 1). The TRPM8 channel responded best to amide coolers. It was noted that the TRPM8 channel also responded to Miracool (ester and amide) and menthyl lactate at ~50% the maximal response of amide coolers. The Givaudan cooler was the most potent cooler known with an $EC_{50}$ of 10 nM. Temporal responses were observed in three classes (FIG. 2). The Givaudan cooler gave a quick response and stayed high, Menthol gave a quick response with deterioration over time and menthyl lactate gave a quick response with a quick loss of signal. Maximal responses showed that the Givaudan cooler gave the highest response followed by menthol. Furthermore, blends of Menthol and WS-3 appeared to synergize (FIGS. 3A and 3B).

The muted response of menthyl lactate has been demonstrated (Behrendt, et al. ((2004) Br. J. Pharmacol. 141:737), wherein a FLIPR-based TRPM8 assay was used to evaluate 70 compounds. It was shown that two types of temporal and maximal responses could be observed, one of which included compounds that responded at 50% the level of menthol. As summarized in Table 1 herein, menthyl lactate (Frescolate ML) falls in to this category.

EXAMPLE 3

TRPA1 FLIPR Analysis

The lack of apparent response of TRPM8 to ester coolers Cooler 2 & Ultracool 7 was unexpected. These data indicated that a secondary mechanism was involved in cooling. McKemy ((2005) *Molecular Pain* 1:16) has suggested that TRPM8 is the moderate cold receptor while TRPA1 is the noxious cold receptor, e.g., at temperatures below 15° C. Thus, it was determined whether the TRPA1 receptor was the receptor for the ester cooler ligands.

The coding sequence for human TRPA1 was obtained from the NCBI public database under GENBANK Accession No. NM_007332. The coding sequence was synthesized and a consensus Kozak sequence was added (GCCACC, SEQ ID NO:3) before the translation start signal to facilitate translation. NotI and XhoI restriction sites were also added to the ends to facilitate cloning into expression vectors. The resulting nucleic acid molecule encoding TRPA1 is set forth herein in SEQ ID NO:2.

The TRPA1 cDNA was cloned into two expression vectors, pcDNA5/FRT and pcDNA5/FRT/TO (INVITROGEN), using the NotI and XhoI sites. The former vector allows for constitutive expression in mammalian cells the latter for inducible expression in same. Restriction digests, ligations and transformations were performed using routine molecular biological techniques, wherein restriction enzymes were obtained from New England Biolabs, a rapid ligation kit from Roche and competent cells (Max Efficiency DH5 t1 phage-resistant) from INVITROGEN.

Bacterial colonies were screened by PCR to identify positive recombinants. Positive bacterial recombinants for each vector were grown in a large culture volume to generate large amounts of vector for transfection. Vector was purified using an endotoxin-free plasmid prep kit (QIAGEN). Both large scale vectors were sequenced completely to verify 100% match to published sequences of TRPA1.

Sequence-verified pcDNA5/FRT-TRPA1 vector and pcDNA5/FRT/TO-TRPA1 vector were individually transfected into TREX FLP-IN HEK 293 mammalian cells (INVITROGEN) using FUGENE 6.0 transfection reagent (Roche) following the manufacturer's protocol. Cells were incubated for 24 to 36 hours with transfection reagent plus vector before being diluted 1:10 into new vessels with media containing 10% FBS only and no antibiotics. Twenty-four hours after dilution of cells, media was changed to that containing 150 µg/ml Hygromycin B and 15 µg/ml Blasticidin HCl. Cells were grown for 10-15 days and media was changed every 2-3 days. At the end of drug selection, cells that had stably taken up vector formed isolated, clonal colonies. Several individual colonies were isolated for each vector transfection and moved to their own tissue culture vessel.

To screen cells for expression of TRPA1 mRNA, the cells were grown for several days until there were enough to perform RT-PCR. For each cell sample, RNA was isolated using RNA-mini kit (QIAGEN) and first-strand cDNA synthesized with SUPERCRIPT III RT kit (INVITROGEN). cDNA from all samples was subjected to PCR using standard protocols and primers specific for TRPA1. Cells that gave positive RT-PCR results were selected for use in assays.

Figure 4:
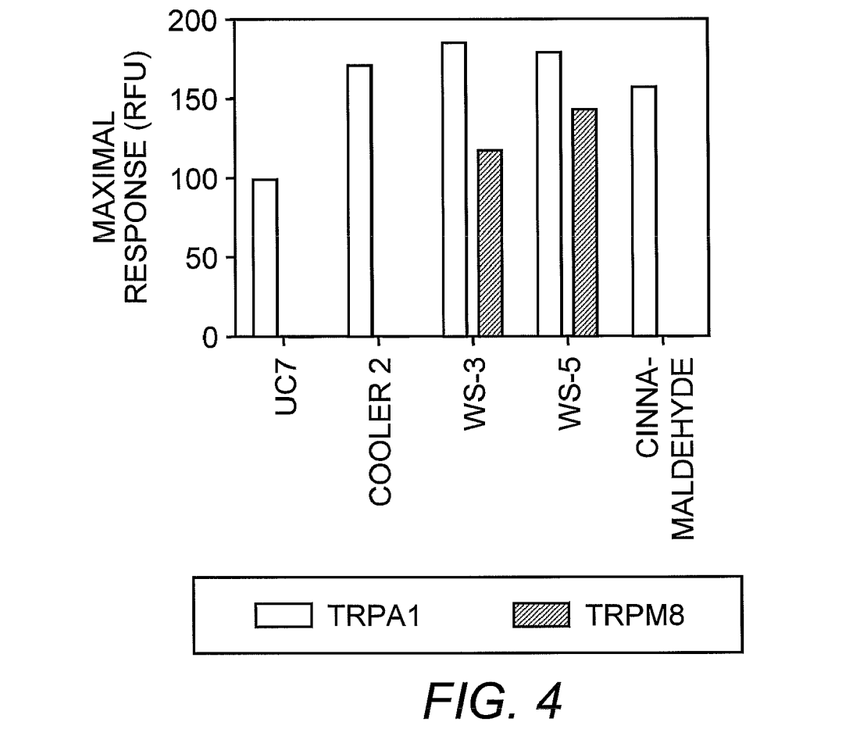
FIG. 4 shows a comparison of the maximal responses of TRPM8 and TRPA1 to Ultracool 7, Cooler 2, WS-3, WS-5 and cinnamaldehyde.
Figure 5:
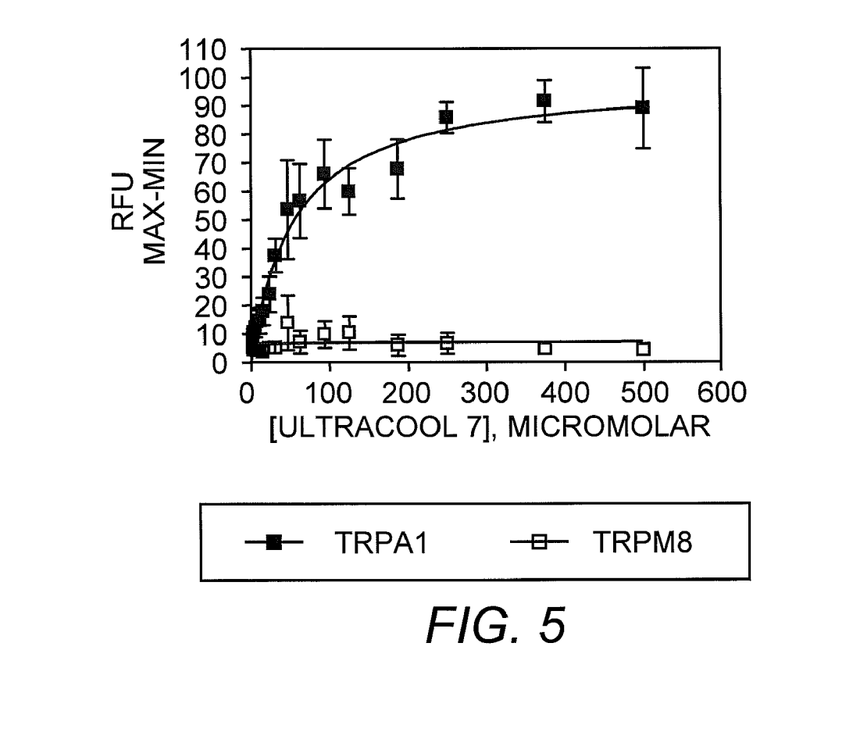
FIG. 5 shows a comparison of the dose responses of TRPM8 and TRPA1 to Ultracool 7.
Figure 6:
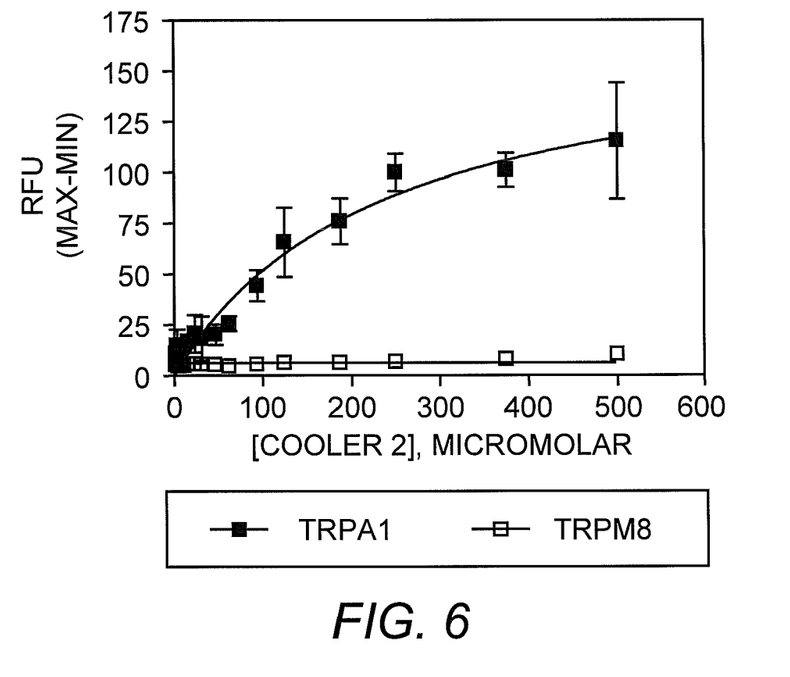
FIG. 6 shows a comparison of the dose responses of TRPM8 and TRPA1 to Cooler 2.
Figure 7:
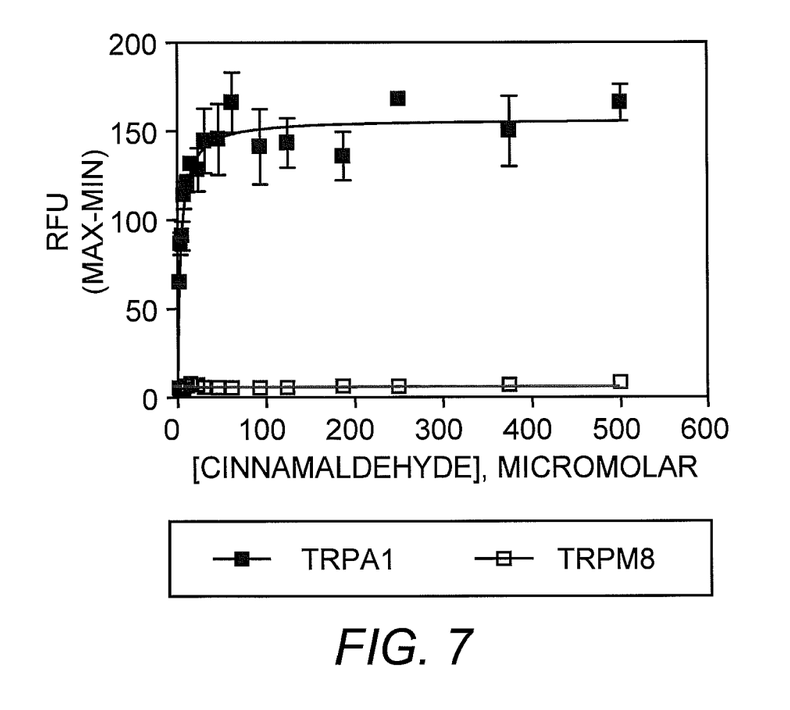
FIG. 7 shows a comparison of the dose responses of TRPM8 and TRPA1 to cinnamaldehyde.
Figure 8:
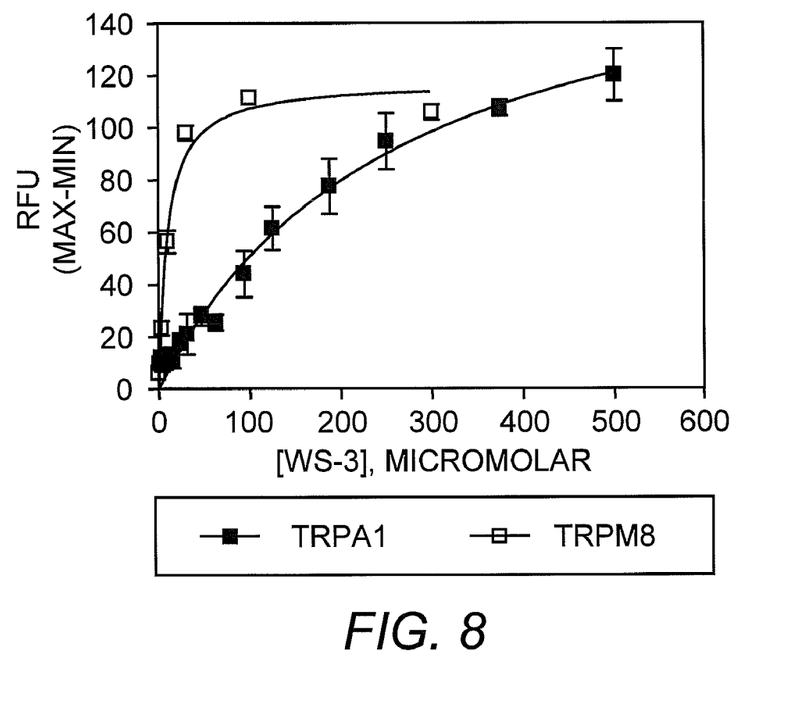
FIG. 8 shows a comparison of the dose responses of TRPM8 and TRPA1 to WS-3.
Figure 9:
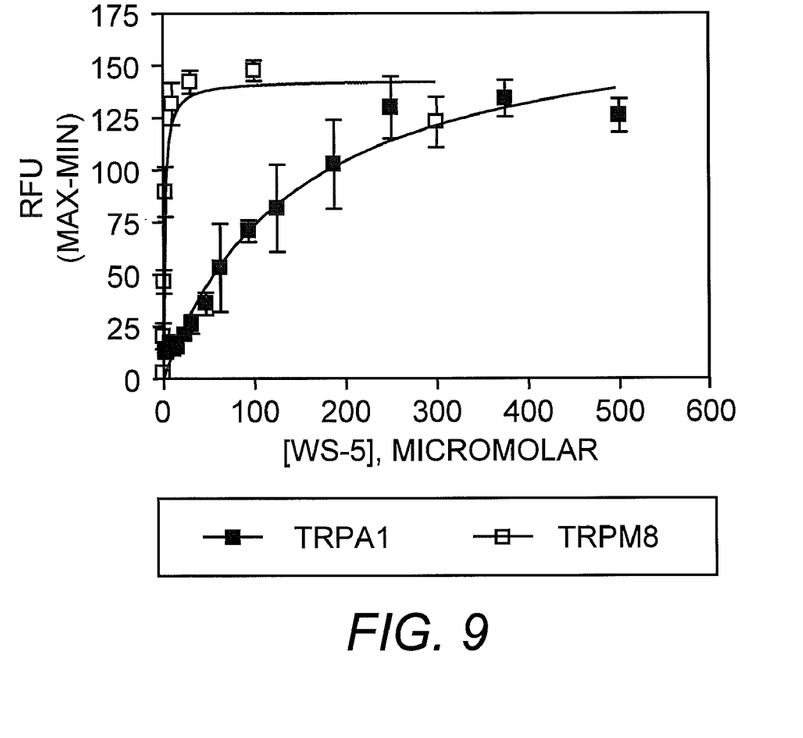
FIG. 9 shows a comparison of the dose responses of TRPM8 and TRPA1 to WS-5.

FLIPR analysis of these cells indicated that cells expressing TRPA1 were more responsive to ester coolers than TRPM8 (FIG. 4). Indeed, in a comparison of TRPA1 to TRPM8 response to Ultracool 7, TRPA1 responded to a wide range of concentrations of Ultracool 7, whereas TRPM8 exhibited no response (FIG. 5). Similar results were obtained for TRPA1 with Cooler 2 (FIG. 6) and cinnamaldehyde (FIG. 7). Moreover, both TRPM8 and TRPA1 responded to WS-3 (FIG. 8) and WS-5 (Figure), with TRPM8 responding better to these coolers.

What is claimed is:

1. A method for identifying an ester cooler comprising contacting a Transient Receptor Potential Cation Channel, Subfamily A, Member 1 (TRPA1) protein in a cell-based assay, with an agent to be tested for potential activity as an ester cooler; determining whether the agent increases or decreases the activity of the TRPA1 protein; selecting for the agent that increases the activity of the TRPA1 protein; determining the cooling strength of said agent that increases the activity of the TRPA1 protein; and organoleptically comparing the cooling strength of said agent that increases the activity of the TRPA1 protein relative to the cooling strength of menthol, whereby an increase in the cooling strength of said agent relative to the cooling strength of menthol thereby identifies said test agent as an ester cooler.

2. The method of claim 1, wherein the Transient Receptor Potential Cation Channel, Subfamily A, Member 1 protein comprises SEQ ID NO:1.

* * * * *

SEQUENCE LISTING

```
<160> NUMBER OF SEQ ID NOS: 2

<210> SEQ ID NO 1
<211> LENGTH: 1119
<212> TYPE: PRT
<213> ORGANISM: Homo sapiens

<400> SEQUENCE: 1

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

Asn Phe Asn Lys Gln Lys Lys Leu Lys Arg Cys Asp Asp Met Asp Thr
    50                  55                  60

Phe Phe Leu His Tyr Ala Ala Ala Glu Gly Gln Ile Glu Leu Met Glu
```

-continued

```
                65                  70                  75                  80
Lys Ile Thr Arg Asp Ser Ser Leu Glu Val Leu His Glu Met Asp Asp
                    85                  90                  95

Tyr Gly Asn Thr Pro Leu His Cys Ala Val Glu Lys Asn Gln Ile Glu
                100                 105                 110

Ser Val Lys Phe Leu Leu Ser Arg Gly Ala Asn Pro Asn Leu Arg Asn
                115                 120                 125

Phe Asn Met Met Ala Pro Leu His Ile Ala Val Gln Gly Met Asn Asn
            130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                    165                 170                 175

Asn Ser Glu Ala Leu Gln Ile Leu Leu Lys Lys Gly Ala Lys Pro Cys
                180                 185                 190

Lys Ser Asn Lys Trp Gly Cys Phe Pro Ile His Gln Ala Ala Phe Ser
            195                 200                 205

Gly Ser Lys Glu Cys Met Glu Ile Ile Leu Arg Phe Gly Glu Glu His
            210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                    245                 250                 255

Met Cys Leu Asp Asn Gly Ala Gln Ile Asp Pro Val Gln Lys Gly Arg
                260                 265                 270

Cys Thr Ala Ile His Phe Ala Ala Thr Gln Gly Ala Thr Glu Ile Val
            275                 280                 285

Lys Leu Met Ile Ser Ser Tyr Ser Gly Ser Val Asp Ile Val Asn Thr
            290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                    325                 330                 335

Lys Ile Asp Ser Glu Gly Arg Ser Pro Leu Ile Leu Ala Thr Ala Ser
                340                 345                 350

Ala Ser Trp Asn Ile Val Asn Leu Leu Leu Ser Lys Gly Ala Gln Val
            355                 360                 365

Asp Ile Lys Asp Asn Phe Gly Arg Asn Phe Leu His Leu Thr Val Gln
            370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                    405                 410                 415

Leu His Tyr Ala Cys Arg Gln Gly Gly Pro Gly Ser Val Asn Asn Leu
                420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
            450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                    485                 490                 495
```

-continued

```
Val Val Gln Leu Leu Lys Lys Gly Ala Leu Phe Leu Ser Asp His
            500                 505                 510

Asn Gly Trp Thr Ala Leu His Ala Ser Met Gly Tyr Thr Gln
        515                 520                 525

Thr Met Lys Val Ile Leu Asp Thr Asn Leu Lys Cys Thr Asp Arg Leu
        530                 535                 540

Asp Glu Asp Gly Asn Thr Ala Leu His Phe Ala Ala Arg Glu Gly His
545                 550                 555                 560

Ala Lys Ala Val Ala Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
            595                 600                 605

Leu Lys Ile Phe Ser His Asn Ser Pro Gly Asn Lys Cys Pro Ile Thr
            610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
        690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
        755                 760                 765

Leu Ile Lys Thr Cys Met Ile Leu Val Phe Leu Ser Ser Ile Phe Gly
        770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
        835                 840                 845

Tyr Leu Gln Arg Phe Glu Asn Cys Gly Ile Phe Ile Val Met Leu Glu
850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910
```

-continued

```
Leu Gly Asp Ile Asn Tyr Arg Glu Ser Phe Leu Glu Pro Tyr Leu Arg
    915                 920                 925

Asn Glu Leu Ala His Pro Val Leu Ser Phe Ala Gln Leu Val Ser Phe
    930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
                980                 985                 990

Trp Phe Leu Arg Lys Val Asp Gln Lys Ser Thr Ile Val Tyr Pro Asn
        995                 1000                1005

Lys Pro Arg Ser Gly Gly Met  Leu Phe His Ile Phe  Cys Phe Leu
    1010                 1015                1020

Phe Cys Thr Gly Glu Ile Arg  Gln Glu Ile Pro Asn  Ala Asp Lys
    1025                 1030                1035

Ser Leu Glu Met Glu Ile Leu  Lys Gln Lys Tyr Arg  Leu Lys Asp
    1040                 1045                1050

Leu Thr Phe Leu Leu Glu Lys  Gln His Glu Leu Ile  Lys Leu Ile
    1055                 1060                1065

Ile Gln Lys Met Glu Ile Ile  Ser Glu Thr Glu Asp  Asp Asp Ser
    1070                 1075                1080

His Cys Ser Phe Gln Asp Arg  Phe Lys Lys Glu Gln  Met Glu Gln
    1085                 1090                1095

Arg Asn Ser Arg Trp Asn Thr  Val Leu Arg Ala Val  Lys Ala Lys
    1100                 1105                1110

Thr His  His Leu Glu Pro
    1115
```

<210> SEQ ID NO 2
<211> LENGTH: 3399
<212> TYPE: DNA
<213> ORGANISM: Artificial sequence
<220> FEATURE:
<223> OTHER INFORMATION: Synthetic nucleic acid

<400> SEQUENCE: 2

```
gcggccgcgc caccatgaag cgcagcctga ggaagatgtg gcgccctgga gaaagaagg      60 agccccaggg cgttgtctat gaggatgtgc cggacgacac ggaggatttc aaggaatcgc     120
ttaaggtggt ttttgaagga agtgcatatg gattacaaaa ctttaataag caaaagaaat     180 taaaagatg tgacgatatg gacaccttct tcttgcatta tgctgcagca gaaggccaaa     240
ttgagctaat ggagaagatc accagagatt cctctttgga agtgctgcat gaaatggatg     300
attatggaaa taccctctg cattgtgctg tagaaaaaaa ccaaattgaa agcgttaagt      360
ttcttctcag cagaggagca aacccaaatc tccgaaactt caacatgatg gctcctctcc     420
acatagctgt gcagggcatg aataatgagg tgatgaaggt cttgcttgag catagaacta     480
ttgatgttaa tttggaagga gaaaatggaa acacagctgt gatcattgcg tgcaccacaa     540
ataatagcga agcattgcag attttgctta aaaaggagc taagccatgt aaatcaaata     600 aatgggata tttccctatt caccaagctg catttcagg ttccaaagaa tgcatggaaa       660
taatactaag gtttggtgaa gagcatgggt acagtagaca gttgcacatt aactttatga     720
ataatgggaa agccaccct ctccacctgg ctgtgcaaaa tggtgacttg gaaatgatca      780
aaatgtgcct ggacaatggt gcacaaatag acccagtgga gaagggaagg tgcacagcca     840
```

```
ttcattttgc tgccacccag ggagccactg agattgttaa actgatgata tcgtcctatt       900
ctggtagcgt ggatattgtt aacacaaccg atggatgtca tgagaccatg cttcacagag       960
cttcattgtt tgatcaccat gagctagcag actatttaat ttcagtggga gcagatatta      1020
ataagatcga ttctgaagga cgctctccac ttatattagc aactgcttct gcatcttgga      1080
atattgtaaa tttgctactc tctaaaggtg cccaagtaga cataaaagat aattttggac      1140
gtaattttct gcatttaact gtacagcaac cttatggatt aaaaaatctg cgacctgaat      1200
ttatgcagat gcaacagatc aaagagctgg taatggatga agacaacgat gggtgtactc      1260
ctctacatta tgcatgtaga caggggggcc ctggttctgt aaataaccta cttggcttta      1320
atgtgtccat tcattccaaa agcaaagata agaaatcacc tctgcatttt gcagccagtt      1380
atgggcgtat caatacctgt cagaggctcc tacaagacat aagtgatacg aggcttctga      1440
atgaaggtga ccttcatgga atgactcctc tccatctggc agcaaagaat ggacatgata      1500
aagtagttca gcttcttctg aaaaaaggtg cattgtttct cagtgaccac aatggctgga      1560
cagctttgca tcatgcgtcc atgggcgggt acactcagac catgaaggtc attcttgata      1620
ctaatttgaa gtgcacagat cgcctggatg aagacgggaa cactgcactt cactttgctg      1680
caagggaagg ccacgccaaa gccgttgcgc ttcttctgag ccacaatgct gacatagtcc      1740
tgaacaagca gcaggcctcc tttttgcacc ttgcacttca caataagagg aaggaggttg      1800
ttcttacgat catcaggagc aaaagatggg atgaatgtct taagattttc agtcataatt      1860
ctccaggcaa taaatgtcca attacagaaa tgatagaata cctccctgaa tgcatgaagg      1920
tacttttaga tttctgcatg ttgcattcca cagaagacaa gtcctgccga gactattata      1980
tcgagtataa tttcaaatat cttcaatgtc cattagaatt caccaaaaaa acacctacac      2040
aggatgttat atatgaaccg cttacagccc tcaacgcaat ggtacaaaat aaccgcatag      2100
agcttctcaa tcatcctgtg tgtaaagaat atttactcat gaaatggttg gcttatggat      2160
ttagagctca tatgatgaat ttaggatctt actgtcttgg tctcatacct atgaccattc      2220
tcgttgtcaa tataaaacca ggaatggctt tcaactcaac tggcatcatc aatgaaacta      2280
gtgatcattc agaaatacta gataccacga attcatatct aataaaaact tgtatgattt      2340
tagtgttttt atcaagtata tttgggtatt gcaaagaagc ggggcaaatt ttccaacaga      2400
aaaggaatta ttttatggat ataagcaatg ttcttgaatg gattatctac acgacgggca      2460
tcattttgt gctgcccttg tttgttgaaa taccagctca tctgcagtgg caatgtggag      2520
caattgctgt ttacttctat tggatgaatt tcttattgta tcttcaaaga tttgaaaatt      2580
gtggaatttt tattgttatg ttggaggtaa ttttgaaaac tttgttgagg tctacagttg      2640
tatttatctt ccttcttctg gcttttggac tcagctttta catcctcctg aatttacagg      2700
atcccttcag ctctccattg ctttctataa tccagacctt cagcatgatg ctaggagata      2760
tcaattatcg agagtccttc ctagaaccat atctgagaaa tgaattggca catccagttc      2820
tgtcctttgc acaacttgtt tccttcacaa tatttgtccc aattgtcctc atgaatttac      2880
ttattggttt ggcagttggc gacattgctg aggtccagaa acatgcatca ttgaagagga      2940
tagctatgca ggtggaactt cataccagct tagagaagaa gctgccactt tggtttctac      3000
gcaaagtgga tcagaaatcc accatcgtgt atcccaacaa acccagatct ggtgggatgt      3060
tattccatat attctgtttt ttattttgca ctggggaaat aagacaagaa ataccaaatg      3120
ctgataaatc tttagaaatg gaaatattaa agcagaaata ccggctgaag gatcttactt      3180
```

```
ttctcctgga aaaacagcat gagctcatta aactgatcat tcagaagatg gagatcatct    3240
ctgagacaga ggatgatgat agccattgtt cttttcaaga caggtttaag aaagagcaga    3300
tggaacaaag gaatagcaga tggaatactg tgttgagagc agtcaaggca aaaacacacc    3360
atcttgagcc ttagctcctc agaccttcag tgactcgag                          3399
```